United States Patent [19]

Devillard

[11] Patent Number: 4,846,393
[45] Date of Patent: Jul. 11, 1989

[54] PROCESS FOR ATTACHING A POROUS LAYER TO A SUBSTRATE AND USING THE PROCESS TO THE MAKING OF A PROSTHESIS

[75] Inventor: Jacques Devillard, Saint Ismier, France

[73] Assignee: Commissariat a l'Energie Atomique, Paris, France

[21] Appl. No.: 148,860

[22] Filed: Jan. 27, 1988

[30] Foreign Application Priority Data

Jan. 28, 1987 [FR] France ................... 87 00991

[51] Int. Cl.[4] .............................................. A61F 1/24
[52] U.S. Cl. .................................................. 228/178
[58] Field of Search ............. 623/16, 18; 228/178, 228/118, 157, 193

[56] References Cited

U.S. PATENT DOCUMENTS

| | | | |
|---|---|---|---|
| 4,040,159 | 8/1977 | Darrow et al. ................. | 228/118 |
| 4,393,987 | 7/1983 | Anderson et al. ............... | 228/157 |
| 4,483,478 | 11/1984 | Schulz ............................. | 228/157 |
| 4,570,271 | 2/1986 | Sump ............................... | 228/193 |
| 4,608,052 | 8/1986 | Van Kampen et al. ......... | 623/18 |
| 4,636,219 | 1/1987 | Pratt et al. ...................... | 228/193 |
| 4,660,755 | 4/1987 | Farling et al. .................. | 228/178 |

*Primary Examiner*—M. Jordan
*Attorney, Agent, or Firm*—Pearne, Gordon, McCoy & Granger

[57] ABSTRACT

A process for attaching a porous layer to a substrate adapted to form the core of a hip prosthesis, the substrate is placed in a cavity in a mould. Spherules are introduced into the space between the substrate and the walls of the cavity. The mould is placed in a furnace, which is heated to a temperature at which the material of which the substrate is made is superplastic. Then a pressure of the order of 10 to 30 MPa is applied to the mould, enabling the spherules to be encrusted on the substrate at a relatively low temperature.

15 Claims, 3 Drawing Sheets

PROCESS FOR ATTACHING A POROUS LAYER TO A SUBSTRATE AND USING THE PROCESS TO THE MAKING OF A PROSTHESIS

BACKGROUND OF THE INVENTION

The invention relates to attaching a porous layer to a dense rigid support and can be particularly advantageously applied to the making of prostheses, more particularly hip prostheses.

The majority of hip prostheses comprise an intramedullary rod sealed to the femur by an acrylic cement. As it sets, the cement causes an exothermic polymerization. A considerable amount of heat is given off and the temperature can locally reach values of teh order of 60° C. This results in an appreciable primary necrosis of the surrounding tissues. Another disadvantage of this kind of prosthesis results from the fact that the doefficient of thermal expansion of the cement, which is ten times higher than that of the adjacent bone tissue, causes on cooling a gap between the bone and the cement which may be as large as several microns in certain places. The cement layer is moreover sintered on to the metal rod of the prosthesis and may become cracked. The resulting debris also sooner or later induces necrosis in the adjoining bone tissue, such necrosis finally leading to the unsealing of the rod.

A number of methods eliminating the use of cement have been suggested to obviate these disadvantages. Generally in these methods scoring or irregular roughnesses are created by milling or moulding on the tail of the femur to increase the contact surface with its medullary canal. This method avoids the use of cement, since the bone tissue directly contacts the prosthesis by rehabitation of the relief thus created, but such rehabitation is unreliable, since generally it does not take place in optimum conditions and remains difficult to control.

Other more reliable methods have been suggested which produce the porous zone by powder metallurgy.

International Pat. No. 83/00282 discloses a process wherein the porous zone is obtained by coating the surface of the prosthesis with a mixture of two different powders, for example, titanium and iron. After partial densification, one of the two powders is eliminated, for example, by dissolution, leaving considerable empty spaces between the grains of the other powder.

European Pat. No. 075378 discloses a process wherein the porous zone is obtained directly by sintering with powders of different grain sizes. A first powder is brought into contact with the surface of the prosthesis corresponding to the tail of the femur, while a second powder is brought into contact with the part of the prosthesis corresponding to the femur head. A judicious selection of the powders and control of the densification parameters enables a porous zone to be obtained on the side of the tail of the femur and a dense zone on the side of its head simultaneously.

Although these two last-mentioned processes are more reliable than the preceding ones, they still have a number of disadvantages, mainly due to the fact that in both cases the porous zone is metallurgically connected to the support by diffusion. However, two phenomena contribute towards the degradation of the mechanical properties of a hip prosthesis rehabitable by the bone tissue when the prosthesis is formed by dense metallic support (which can be formed by titanium, a titanium alloy or a cobalt- or iron-based alloy) and a porous coating adhering to the surface of the supprt. Elevated temperatures (of the order of 1150 to 1450° C.) are required for producing the connection between the support and the coating, more particularly in the case of titanium alloys, which are the ones most widely used. Such temperatures lead to a considerable enlargement of the $\beta$ grain and the formation of an $\alpha$ grain joint, something which degrades the mechanical characteristics of the support. This sintering temperature can be reduced by means of sintering adjuvants (for example, copper or silver), and this causes a local displacement of the transition temperature between the $\alpha/\beta$ structure and the $\beta$ structure. This contributes towards the creation of a connecting layer of $\beta$ structure. The change in structure increases sensitivity to the propagation of cracks in the titanium alloys which are moreover highly sensitive to the notching effect—i.e., the start of a crack.

However, a metallurgical connection of a spherule to a titanium alloy support is equivalent to a notch machined in a smooth support. This is illustrated by the annexed FIG. 1, which shows a spherule 10 metallurgically connected to a substrate 12. It can be seen that the spherule 10 is attached to the substrate 12 via a neck 14 of very small radius. Since diffusion has taken place between the spherule and the substrate, everything takes place as if this were a single object in which a notch having the shape of the neck 14 had been produced.

The equivalent coefficient of stress intensity $K_t$ will be higher in proportion to the smallness of the connecting radius or the fritting neck between the spherule and the support.

This geometry is observed in processes using natural sintering (without external stresses) with or without sintering adjuvant. If such an adjuvant is used, the temperature of appearance of the first liquid higher than the temperature of conversion of the $\alpha$ structure into the $\beta$ structure contributes towards the formation of $\alpha$ grain joints on cooling in the forged support and towards a partial dissolution in the spherules forming the porous zone. The formation of small $\alpha$ plaquettes extending through the diffusion zone (reference 16 in FIG. 1) contributes towards the fragility of the connection under stressing. In the case of a porous layer connected to a titanium alloy support, the problem arises of the presence of notches in a structure particularly unfavorable to the strength of the support. The reduction in the mechanical characteristics of such composite elements is considerable, with a limit of endurance which may be only 20% of that measured in such alloys when the experiment is performed with smooth test pieces.

It is an object of the invention to obviate these disadvantages by providing a process for attaching a porous layer to a substrate which can be used more particularly for making prostheses and which enables the spherules to be readily attached to and satisfactorily retained on the support.

SUMMARY OF THE INVENTION

According to the main feature of the process according to the invention, the substrate being made of a first material and the porous layer being made of a second material, the process comprises the following stages:

(a) putting the substrate in conditions in which the first material is superplastic, and (b) sintering the porous layer on to the substrate so that the layer becomes at least partially encrusted on the surface of the substrate.

Preferably the first and second materials belong to the group formed by titanium, cobalt, chromium, tantalum and their alloys.

According to another feature of the invention, the porous layer is formed by spherules whose diameter is between 100 and 1000 microns, preferably between 500 and 600 microns.

When the first material is titanium, the stage (b) is performed at a temperature of between 700 and 950° C., preferably 825° C. If other metals or alloys are used, an engineer in the art can select other temperatures, the essential thing being that the first material must be superplastic at the temperature used.

The pressure at which the stage (b) is performed is between 10 and 30 MPa, preferably 20 MPa.

Advantageously the process can comprise an extra stage (c), performed before the stage (b) and consisting in creating an antidiffusion barrier on the surface of the substrate. The antidiffusion barrier can be obtained by creating an oxide layer on the surface of the substrate.

The process can also comprise an extra stage (d), performed before the stage (b) and consisting of sintering the porous layer outside the substrate at an elevated temperature, resulting in the spherules diffusion bonding to one another at all points of contact between them, attachment to the substrate being performed during a second thermal treatment formed by the stage (b) when the first material is in its range of superplasticity. When the second material is titanium, the stage (d) is performed at a temperature of between 1000 and 1450° C., preferably 1250° C. If another metal or alloy is used, the stage (d) will be performed at a temperature at which the porous layer can be sintered, resulting in the spherules diffusion bonding to one another at all points of contact between them outside the substrate.

Lastly, the process can be particularly advantageously applied to the making of prostheses, more particularly the making of hip prostheses.

A few familier notions of metallurgy will also be recalled which relate to what is currently called the superplastic state. For a given metal the superplastic state can be fully reproduced and controlled. It depends on the treatments given to the material during its production. For example, powders of titanium or one of its alloys having a needleshaped structure have no range of superplasticity. In contrast, a test piece of titanium or one of its alloys obtained by casting and then dressed or laminated has a structure with fine equiaxed grains which gives it the property of superplasticity in a range of temperature. This is familiar to an engineer in the art. For example, the titanium sheets mentioned in European Pat. No. 191182 are superplastic materials.

The existence of this property is not only due to the nature of the material but also to the metallurgical treatments which it is given.

According to the invention the support must be a material possessing this property. The material of the spherules forming the porous layer has no range of superplasticity. The spherules are a crude product of atomization in vacuo.

BRIEF DESCRIPTION OF THE DRAWING

The invention will be more clearly understood from the following purely illustrative non-limitative exemplary description, with reference to the accompanying drawings, wherein.

DESCRIPTION OF THE PREFERRED EMBODIMENTS

As pointed out above, the process according to the invention mainly consists in placing the substrate in conditions in which the material from which it is made is superplastic and sintering spherules on to the substrate while it is in its superplasticity range.

Within certain intervals of temperature, materials such as titanium or titanium alloys are superplastic—i.e., they can undergo deformations of considerable amplitude under low stress at relatively low temperatures. In the case of titanium and its alloys these temperatures are of the order of 700 to 1000° C., so that they can be deformed under low stress at relatively low temperatures. The deformations enable the porous structure (which is preferably formed by a stack of spherules) to be mechanically anchored by a phenomenom of encrustation by spherule caps. The encrustation is produced without diffusion between the spherules and the support by disposing thereon an antidiffusion barrier formed, for example, by an oxide layer.

Figure 1:
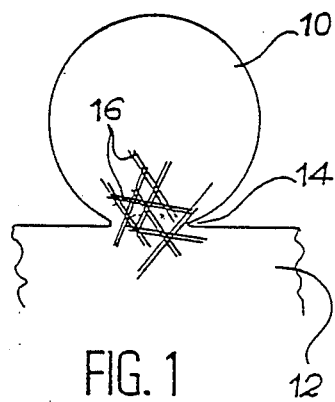
FIG. 1 is a diagrammatic view to an enlarged scale showing a spherule attached to a substrate by the prior art methods of attaching porous layers.
Figure 2:
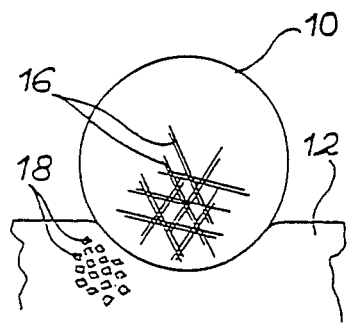
FIG. 2 is a view similar to FIG. 1, showing what is obtained by the process according to the invention.

The result obtained is illustrated in FIG. 2, which shows the spherule 10 attached to the substrate 12. However, contrary to what happens in the case of FIG. 1, there is no metallurgical connection between the spherule 10 and the substrate 12. The spherule has been in some sort pushed into a hole which has been created in the surface of the substrate, due to the fact that the latter is superplastic at the temperatures used. The spherule 10 is therefore in contact with the substrate over a zone which has the shape of a spherical cap. Since there has been no diffusion between the spherules and the substrate, the metallurgical structure of the spherules is different from that of the substrate. The absence of diffusion is due to the fact that a diffusion barrier has been created on the surface of the substrate, for example, by creating an oxide layer before sintering the porous layer. FIG. 2 shows how small plates 16 of α structure are solely inside the spherule and not in a zone straddling the spherule and the substrate. The substrate has a superplastic equiaxed structure formed by grains 18.

The superplastic deformation of a metal or an alloy depends at one and the same time on the size of the grain forming the microstructure and the factor of the shape of such grains. In the case of biphase alloys such as titanium alloys, superplastic deformation also depends on the volumetric concentrations of the phases present.

Figure 3:
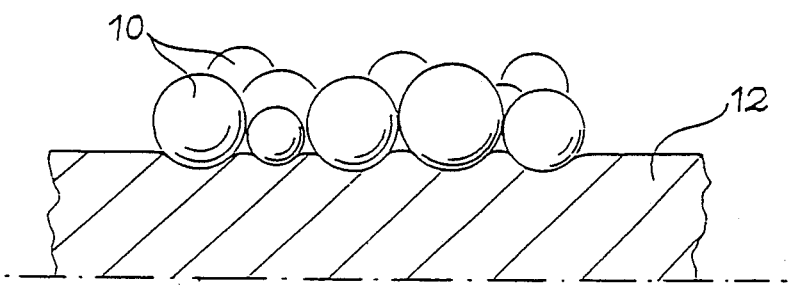
FIG. 3 is a diagrammatic sectional view to an enlarged scale showing a first way of disposing the porous layer formed by spherules on a substrate.
Figure 4:
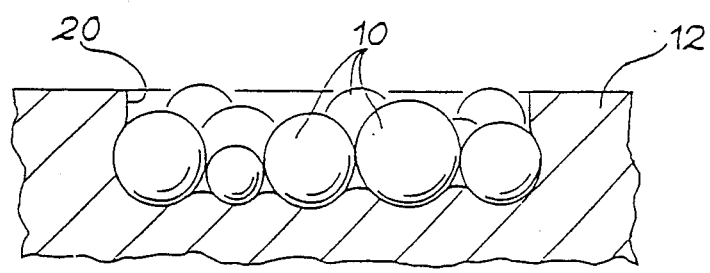
FIG. 4 is a view similar to FIG. 3, illustrating another way of placing the porous layer on the surface of the substrate.

FIGS. 3 and 4 illustrate the two main ways of disposing the porous layer on the substrate 12 when the latter is cylindrical, for example, when it is the core of a hip prosthesis. In the case of FIG. 3, the porous layer has the form of a cylindrically conical ring enclosing the core of the prosthesis. The porous layer is sintered directly on to the surface of the substrate without the latter being previously machined. The encrustations are adequate to prevent shearing ruptures.

In the case shown in FIG. 4 the porous structure is not placed directly on the surface of the substrate 12, but in a cavity or countersinking 20 made in the surface of the substrate. In this case sintering is again performed, but the porous layer is anchored by crimping the assembly of spherules 10 in the recess 20. The depth of the cavity 20 from the surface of the substrate 12 is of the order of 0.5 to 2 mm. If the substrate 12 is the core of a hip prosthesis, the diameter is of the order of 10 to 20 mm.

When fine-grained titanium alloys are used for making the substrate 12, stage (b) of the process—i.e., the sintering of the porous layer while the substrate is in its superplacticity range—is performed at a temperature of between 700 and 950° C. Sintering is performed in moulds made for this operation and reproducing the shape of the composite which is to be obtained. A stress of 10 to 30 MPa is exerted on the mould, on the one hand to connect the spherules to one another, and on the other to deform the support in the zones where it is in contact with the porous structure. It should be noted that although there is no diffusion between the spherules in contact with the substrate and the latter, due to the creation of an antidiffusion barrier, there is diffusion between one spherule and its neighbors, and therefore the spherules are connected to one another by diffusion.

To attach the porous layer to the substrate, either the spherules can be sintered directly on to the substrate after it has been heated to a temperature at which it is superplastic, or a first sintering can be performed outside the substrate at an elevated temperature (between 1000 and 1450° C.) and the spherules attached to the substrate during the course of a second thermal treatment, which is none other than the stage (b)—i.e., a second sintering when the substrate is in its superplasticity range.

The process according to the invention applies mainly to the making of prostheses, more particularly rehabitable hip prostheses. In that case the core of the prosthesis can be obtained by forging in the form of a blank able to receive the porous zone in excess thickness. The core can be formed by a cylindrical bar bent in accordance with the curvature of the prosthesis around which the porous structure will subsequently be attached.

Figure 5:
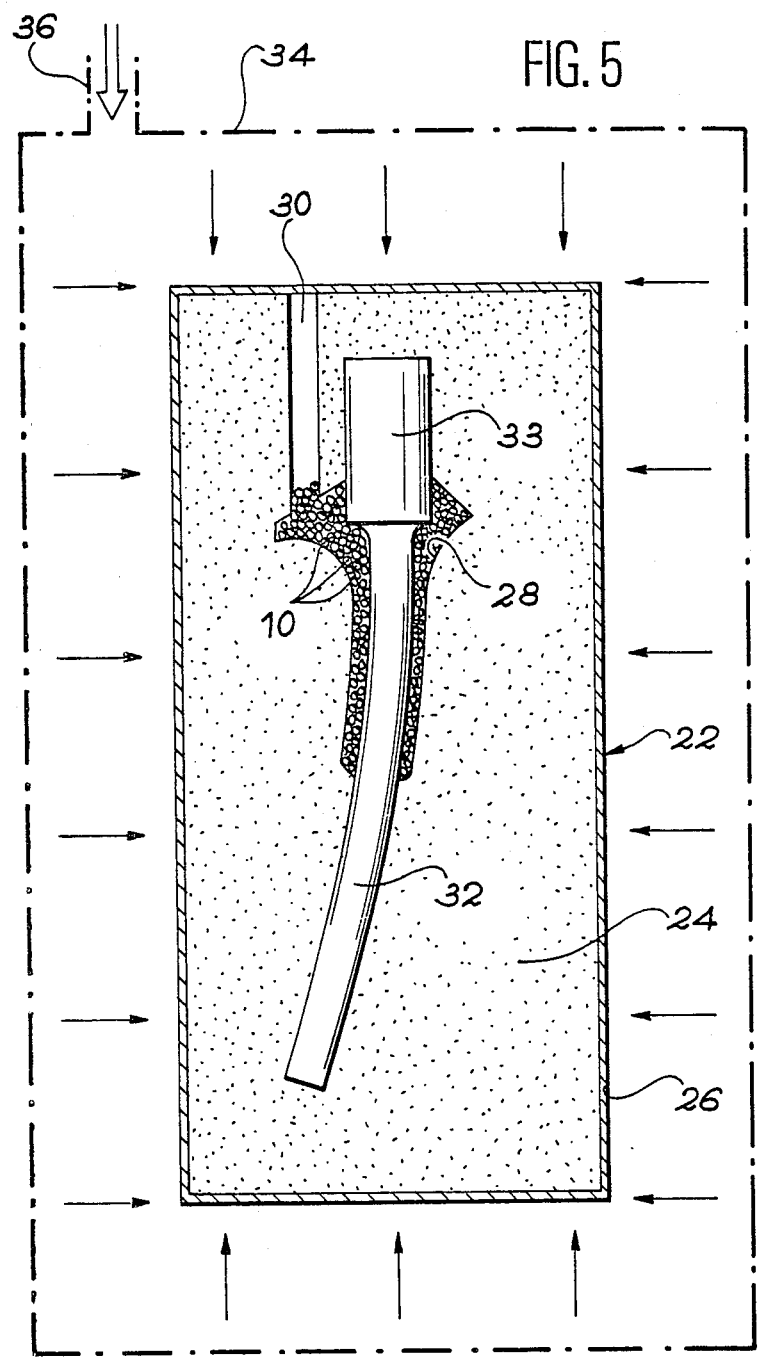
FIG. 5 is a diagrammatic sectional view showing a mould placed in a furnace for the performance of the process according to the invention.

FIG. 5 illustrates a mould which can be used for performing the process according to the invention. As can be seen, the mould 22 mainly comprises a ceramic body 24 disposed in a metal envelope 26 which can be, for example, of hermetic mechanically welded steel. The ceramic body 24 has a cavity 28 whose shape is that of the prosthesis to be obtained. The cavity 28 communicates with the outside of the envelope 26 via a channel 30. First the core 32 of the prosthesis is produced and placed in the cavity 28 of the mould. there is a space between at least a portion of the core 32 and the walls of the cavity. The spherules 10 are introduced via the channel 30 until they fill the whole space between the core 32 and walls of the cavity. If necessary, the particles are descaled prior to sintering. After degassing in vacuo, the mould 22 is placed in an autoclave 34 shown diagrammatically in chain-dot lines in FIG. 5. A conduit 36 enables a pressurized gas, for example, argon, to be introduced into the autoclave 34 to perform the sintering of the porous layer while the core 32 is in its superplasticity range.

A hip prosthesis can be produced by the process according to the invention, using a device such as that shown in FIG. 5, in the following manner:

First the core 32 is produced by bending a forged Ti6Al4V bar of diameter 10 mm in accordance with the shape of the prosthesis to be obtained. A femoral head 33 which will be subsequently machined is provided by sciving. The core is placed in a ceramic mould, like that shown in FIG. 5, having no reactivity at 1000° C. with the material forming the substrate and the porous layer. The open porosity of the mould is between 50 and 70%. Then particles of titanium or titanium alloy Ti6Al4V are introduced into the cavity 28. The particles are spherical and have a diameter of between 100 and 1000 microns, preferably between 500 and 600 microns, since such dimensions enable an open porosity to be obtained which is particularly favorable to osteogenesis. Prior to being placed in the cavity, the particles are descaled in a fluoronitric solution for 20 minutes, then rinsed with ethyl alchohol and dried. It should be noted that the core 32 can be used either in the raw state as milled, or be oxidized by the controlled oxidation of its surface. After degassing in vacuo the mould 22 is placed in the autoclave 34 at an argon pressure of 20 MPa for 4 hours to produce the deformation of the substrate and the encrustation of the porous zone, and also the interconnection by diffusion of the titanium alloy particles.

Figure 6:
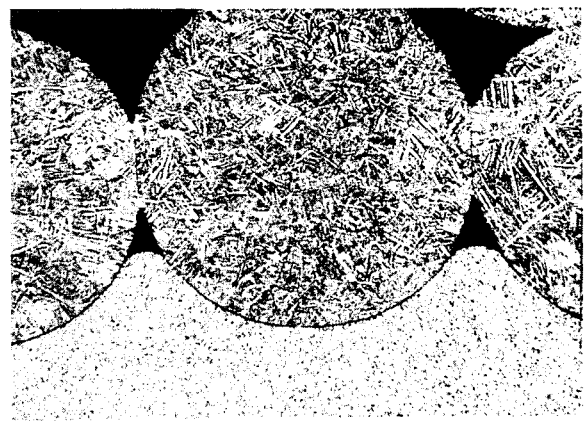
FIGS. 6, 7 and 8 are metallographic sections illustrating the differences between the process according to the invention and the prior art techniques.

FIGS. 6 illustrates according to the invention an encrustation of spherules in the superplastic range of a support—i.e., with fine grains obtained by forging. There is no metallurgical connection between the spherules and the support, which is of forged Ti6Al4V alloy, with a fine equiaxed α crystalization. The quality of the encrustation shows clearly that the superplastic state of the support during the performance of the process can be clearly identified.

Figure 7:
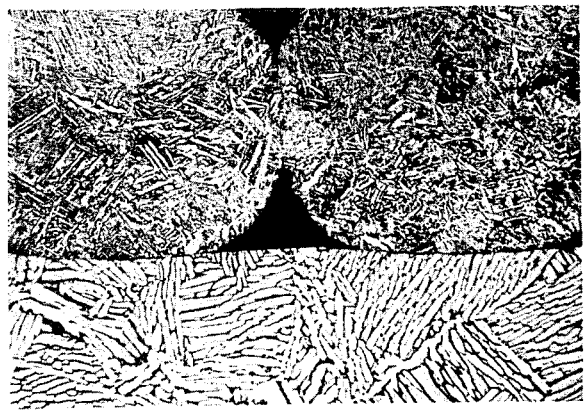
Figure 8:
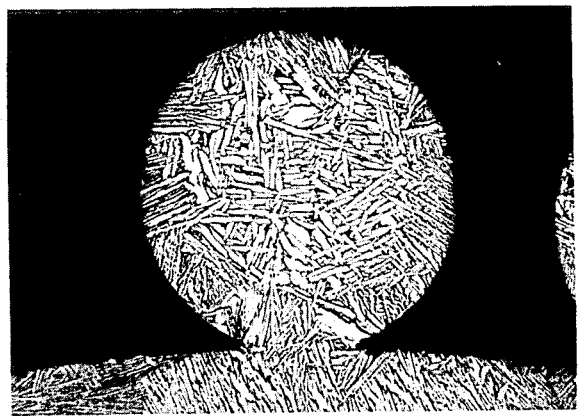

FIG. 7 relates to a support of sintered Ti6A14V alloy crystallized in "wicker-work" fashion in the α system. The drawing shows clearly how the encrustation cannot be obtained in a support which does not have the superplastic characteristics—i.e., with coarse grains obtained by sintering (the thermomechanical treatment conditions allowing the production of the structures illustrated in FIGS. 6 and 7 are identical). FIG. 8 shows the connection of a particle to a support by silver soldering. The support consists of forged Ti6Al4V alloy which has caused a transformed acicular β crystallization. The metallographic section shows clearly a metallurgical continuity between the structure of the spherules and the support, whatever the structure of the latter may be. In this case the support is rendered fragile by a notching effect familiar with titanium alloys.

The two last FIGS. 7 and 8, which do not belong to the invention, enable its originality to be immediately understood.

Thus, the process according to the invention has particular advantages, since it enables spherical particles to be encrusted reliably and durably in a substrate while obviating all risks of fragility which existed with the prior art methods. This is particularly advantageous in the field of prostheses, more particularly hip prostheses, since there is no risk that the porous layer will come away from the substrate to which it is attached.

Lastly, the invention is of course not limited merely to the embodiment thereof which has been disclosed hereinbefore, but variants may be envisaged without exceeding the scope of the invention. For example, an engineer in the art can modify the device used and the experimental conditions, on condition that the substrate is heated to a temperature range in which it is superplastic. Lastly, although the invention is mainly used for making prostheses, the process applies equally to all fields in which a porous layer must be attached to a substrate.

I claim:

1. A process for attaching a porous layer to a substrate, the substrate being made of a first material and the porous layer of a second material, characterized in that said process comprises the following stages:
   (a) putting the substrate in conditions in which the first material is superplastic, and
   (b) sintering the porous layer on to the substrate so that the layer becomes at least partially encrusted on the surface of the substrate.

2. A process according to claim 1, characterized in that the first material belongs to the group formed by titanium, cobalt, chromium, tantalum and their alloys.

3. A process according to claim 1, characterized in that the second material belongs to the group formed by titanium, cobalt, chromium, tantalum and their alloys.

4. A process according to claim 1, characterized in that the porous layer is formed by spherules.

5. A process according to claim 4, characterized in that the diameter of the spherules is between 100 and 1000 microns.

6. A process according to claim 5, characterized further that the diameter is preferably between 500 and 600 microns.

7. A process according to claim 1, characterized in that the first material being titanium, stage (b) is performed at a temperature of between 700 and 950° C., preferably 825° C.

8. A process according to claim 1, characterized in that the stage (b) is performed at a pressure of between 10 and 30 MPa, preferably 20 MPa.

9. A process according to claim 1, characterized in that it comprises an extra stage (c), performed before stage (b) and consisting in creating an antidiffusion barrier on the surface of the substrate.

10. A process according to claim 9, characterized in that the stage (c) is performed by creating an oxide layer on the surface of the substrate.

11. A process according to claim 1, characterized in that it comprises an extra stage (d), performed before the stage (b) and consisting of sintering the porous layer outside the substrate at an elevated temperature, resulting in the second material diffusion bonding at all points of contact amongst itself.

12. A process according to claim 11, characterized in that the second material being titanium, the stage (d) is performed at a temperature of between 1000 and 1450° C., preferably 1250° C.

13. A process according to claim 1, wherein the properties of the second material and first material are selected so they will promote diffusion bonding at all points of contact amongst the second material with itself and the partial embedding of said second material into said first material.

14. A process according to claim 1, characterized in that the porous layer is formed by a stack of or a multiplicity of layers of the second material, said second material being diffusion bonded together at all points of contact amongst itself, and said porous layer forming a ring which encompasses a preselected surface area of the substrate.

15. A process for attaching a porous layer to a substrate, the substrate being made of a first material and the porous layer of a second material, characterized in that said process comprises the following stages:
   (a) putting the substrate in conditions in which the first material is superplastic, and
   (b) sintering the porous layer onto the substrate so that the layer becomes at least partially encrusted on the surface of the substrate, said porous layer being formed by spherules.

* * * * *